United States Patent [19]
Alas

[11] Patent Number: 5,824,820
[45] Date of Patent: Oct. 20, 1998

[54] PROCESS FOR THE PREPARATION OF CITRACONIC ANHYDRIDE

[75] Inventor: Michel Alas, Melle, France

[73] Assignee: Rhone-Poulenc Chimie, Courbevoie Cedex, France

[21] Appl. No.: 668,027

[22] Filed: Jun. 19, 1996

[30] Foreign Application Priority Data

Jun. 21, 1995 [FR] France ................................. 95 07395

[51] Int. Cl.⁶ .......................... C07C 51/56; C07C 45/66; C12P 17/04
[52] U.S. Cl. .......................... 562/895; 568/355; 435/126
[58] Field of Search ........................... 568/355; 435/126; 562/895

[56] References Cited

U.S. PATENT DOCUMENTS

| | | | |
|---|---|---|---|
| 2,385,283 | 9/1945 | Kane et al. | 195/36 |
| 2,966,498 | 12/1960 | Humphrey | 260/346.8 |
| 5,231,016 | 7/1993 | Cros | 435/142 |
| 5,457,040 | 10/1995 | Jarry et al. | 435/142 |

FOREIGN PATENT DOCUMENTS

| | | | |
|---|---|---|---|
| 0 495 544 | 7/1992 | European Pat. Off. | C07D 207/448 |
| 0 665 211 | 8/1995 | European Pat. Off. | |
| 827638 | 2/1960 | United Kingdom. | |
| 1147308 | 4/1969 | United Kingdom | C07C 51/48 |
| 94/21589 | 9/1994 | WIPO | C07C 57/155 |
| WO 21589 | 9/1994 | WIPO. | |
| 95/06026 | 3/1995 | WIPO | C07C 57/13 |
| WO 06026 | 3/1995 | WIPO. | |

*Primary Examiner*—Allen J. Robinson
*Assistant Examiner*—Barbara Badio
*Attorney, Agent, or Firm*—John Daniel Wood

[57] ABSTRACT

The present invention relates to a novel process for the preparation of citraconic anhydride. More precisely, the invention relates to a process for the preparation of citraconic anhydride from a starting material comprising itaconic acid.

The process for the preparation of citraconic anhydride may be performed continuously starting from itaconic acid, or continuously or in a batchwise manner starting directly from a fermentation broth of itaconic acid or of by-products from the manufacture of itaconic acid.

5 Claims, No Drawings

PROCESS FOR THE PREPARATION OF CITRACONIC ANHYDRIDE

The present invention relates to a novel process for the preparation of citraconic anhydride. More precisely, the invention relates to a process for the preparation of citraconic anhydride from a starting material comprising itaconic acid.

In a variant of the invention, citraconic anhydride is prepared directly from the fermentation broth of itaconic acid or from by-products in the manufacture of itaconic acid.

Citraconic anhydride is a product in increasing demand in industry. It has for several decades formed the subject of much research in order to define the most economical processes for its manufacture.

The most advantageous routes consist in using itaconic acid, generally obtained by fermentation, from renewable starting materials (various sugars, starches, etc.), carrying out an anhydride formation reaction coupled to an isomerization reaction.

U.S. Pat. No. 827,638 thus mentions the preparation from itaconic acid, the dehydration/isomerization reaction being carried out in a batchwise manner under reduced pressure at temperatures of between 155° C. and 185° C.

In order to improve the reaction yield, it has been proposed to use a catalyst in order to accelerate the isomerization reaction. Thus, for example, patent U.S. Pat. No. 2,966,498 describes the manufacture of citraconic anhydride from itaconic acid, using a catalyst based on alkali metal sulphate and dihydrogenophosphate.

The said process is advantageous since the citraconic anhydride is obtained in a single step, but it suffers from several drawbacks. The temperature is difficult to control. The water formed, in small amount during the reaction, is difficult to remove and its distillation also entrains citraconic anhydride, which leads to a loss of the product obtained.

Since the chemical nature of the catalyst can give rise to various problems, namely stability and solubility problems, other high-performance catalytic systems which can be used in the lowest possible amounts have been sought so as not to cause any degradation and to reduce the technological problems.

Thus, Galanti et al. have shown the advantage of using bases as catalyst in order to isomerize itaconic anhydride to citraconic anhydride [J. Org. Chem. 47, 1572–1574, (1982)]. The drawback of this synthesis is two-fold, since the itaconic anhydride must first be made from itaconic acid. In addition, amines are well known to be capable of triggering violent polymerizations of citraconic anhydride, which in industrial terms is a considerable nuisance for the manufacture of this product in total safety.

In order to improve the yields and to reduce the risks associated with the use of amines, the Applicant has proposed, in its French patent application No. 94/00938, new catalytic systems, namely acid-base catalysts having a pKa of between 4 and 10.

In its continued research, the Applicant has improved the process for the preparation of itaconic acid.

A first subject of the invention is the preparation of itaconic acid in a continuous process.

More precisely, the subject of the present invention is a continuous process for the preparation of citraconic anhydride, characterized in that it consists in continuously introducing itaconic acid or a starting material comprising it, and optionally a catalyst, into the reaction medium maintained at a temperature such that the itaconic acid is liquid under the reaction conditions.

The continuous preparation process is very advantageous when it involves the production of large amounts of citraconic anhydride. The size of a continuous reactor carrying out the same production is, in fact, much smaller than that of a reactor which carries it out under batchwise conditions.

In addition, the fact that the reaction is carried out continuously is beneficial in terms of the yield, resulting in a saving on the production costs, and especially a constant quality of the product obtained (reduction of the formation of by-products).

In accordance with the process of the invention, the starting material used is pure itaconic acid or any other itaconic source whose nature is subsequently specified.

The dehydration/isomerization reaction, which is carried out to obtain the citraconic anhydride from itaconic acid, may be carried out in the absence of any solvent or in the presence of a solvent.

Thus, the starting material is introduced continuously into the reaction medium in solid form or in solution in water or in an organic solvent.

The choice of solvent is determined according to its ability to solubilize the starting itaconic acid.

Furthermore, the solvent must be inert under the reaction conditions.

A liquid which forms with water a binary azeotrope whose boiling point is generally at least 130° C. is preferably used as organic solvent. The said organic solvent is chosen such that the binary azeotrope it forms with water has a boiling point lower than:
- the boiling point of citraconic anhydride,
- the boiling point of the binary azeotrope which the citraconic anhydride would be capable of forming, either with water or with the organic solvent itself.

Lastly, the organic solvent is preferably chosen such that it does not form a ternary azeotrope with citraconic anhydride and water, so as to limit the losses of the said anhydride.

The organic solvents which may be used in the context of the process of the invention preferably have boiling point of between 110° C. and 200° C., preferably of from 130° C. to 170° C.

Non-limiting examples which may be mentioned are:
- aliphatic hydrocarbons and more particularly paraffins such as, in particular, octane, isooctane, nonane, decane, undecane and tetradecane; aromatic hydrocarbons such as, in particular, toluene, xylenes, ethylbenzene, diethylbenzenes, trimethylbenzenes, cumene, pseudocumene and petroleum fractions consisting of a mixture of alkylbenzenes, in particular fractions of the Solvesso® type,
- chlorinated aliphatic hydrocarbons such as, for example, 1,1,2-trichloroethane, pentachloroethane, 1-iodo-2-methylpropane, 1-chlorohexane and 1-chloro-2-ethylhexane; chlorinated aromatic hydrocarbons and more particularly chlorobenzene and chlorotoluenes,
- ethers and more particularly aliphatic ethers such as butyl ether, isobutyl ether, ethyl hexyl ether, 1-butoxy-2-methoxyethane, 1,1-diethoxybutane, amyl ether, isoamyl ether and dipropoxymethane; aromatic ethers such as phenyl propyl ether and mesityl oxide,
- nitro compounds such as nitropropane and nitrobenzene,
- aliphatic, cycloaliphatic or, preferably, aromatic ketones, methyl ethyl ketone, methyl isobutyl ketone, diisobutyl ketone, methyl n-amyl ketone, methyl isoamyl ketone, cyclohexanone, methylcyclohexanone and diacetone alcohol.

A mixture of organic solvents may be used.

Among the abovementioned solvents, aromatic hydrocarbons are preferably chosen, and more especially cumene and pseudocumene.

The itaconic acid concentration in the reaction mixture (itaconic acid+reaction solvent) is not critical. Usually, the acid used represents from 10 to 100%, preferably from 10 to 50%, of the weight of the reaction solvent.

According to a variant of the invention, the dehydration/isomerization reaction is carried out in the presence of a catalyst.

Preferably an at least partially organic acid-base catalyst having a pKa of between 4 and 10 is used in the dehydration/isomerization reaction, this catalyst forming the subject of French patent application No. 94/00938.

The choice of the catalyst makes it possible to obtain citraconic anhydride directly from itaconic acid.

A first requirement which presides over the choice of catalyst is that it is a salt which has a pKa of between 4 and 10, preferably of between 5 and 9: the pKa is defined as the cologarithm of the dissociation constant of the acid measured, in aqueous medium, at 25° C.

Another characteristic of the catalyst used in the process of the invention is that it can be fused or melted in the reaction mass. It is important that its melting point be preferably below 200° C., and more preferably below or equal to 180° C.

As mentioned above, the catalyst combines an acid and a base, with at least one of the two being an organic compound.

The catalyst may be a salt resulting from the reaction of an acid and a base, which may be prepared at the time of use.

The stoichiometrically required amounts of acid and base are generally used to form the salt.

This catalyst may also be a salt prepared in situ, by addition of an acid and a base or alternatively by addition only of base, the salt obtained resulting from the reaction of the itaconic acid reactant and the base.

The catalyst thus results from the reaction of an inorganic or organic acid and a base.

Non-limiting examples of such acids which may be mentioned are halogenated acids such as hydrochloric acid, hydrobromic acid and hydrofluoric acid; oxyacids which may or may not be halogenated, such as sulphuric acid, pyrosulphuric acid, perchloric acid and phosphoric acid; sulphonic acids which may or may not be halogenated, such as fluorosulphonic acid, chlorosulphonic acid, trifluoromethanesulphonic acid, methanesulphonic acid, ethanesulphonic acid, ethanedisulphonic acid, benzenesulphonic acid, benzenedisulphonic acids, toluenesulphonic acids, naphthalenesulphonic acids and naphthalenedisulphonic acids.

Among these acids, sulphuric acid, hydrochloric acid, hydrobromic acid, phosphoric acid, trifluoromethanesulphonic acid, para-toluenesulphonic acid and methanesulphonic acid will preferably be used.

Itaconic acid may also be involved in the preparation of the catalyst or of other carboxylic acids which are non-volatile under the reaction conditions.

As regards the base, this is a compound which is an electron-pair donor.

Use may be made of primary, secondary or tertiary nitrogen-containing bases and mention may be made more particularly of:

ammonia;

primary amines such as n-propylamine, isopropylamine, isobutylamine, n-butylamine, tert-butylamine, n-pentylamine, 2-methylbutylamine, 3-methylbutylamine, n-hexylamine, 2-ethylhexylamine, aniline, laurylamine, cyclohexylamine, cyclopentylamine, benzylamine, guanidine, acetamidine, ethanolamine, ethylenediamine, hexamethylenediamine, N-aminoethylpyrrolidine, pyrazoline, N-aminomorpholine, N-aminopiperidine and tetraethylenepentamine;

secondary amines such as dibutylamine, dipropylamine, methylpropylamine, methylbutylamine, methylisobutylamine, methyl-tert-butylamine, methylbenzylamine, di-tert-butylamine, diethanolamine, 1-methylcyclopentylamine, 1-methyl cyclohexylamine, dicyclohexylamine, morpholine, imidazole, pyrrolidine, imidazolidine, piperazine and indole;

tertiary amines such as triethylamine, tributylamine, dimethylaniline, pyridine, pyrazine, triethanolamine, tris(3,6-dioxaheptyl)amine and 1,8-diaza(5.4.0) bicyclo-7-undecene.

Among all the abovementioned nitrogen-containing compounds, saturated or unsaturated heterocyclic nitrogen-containing tertiary bases are preferably chosen, and preferably pyridine or pyrazine. It is also possible to use substitution derivatives ($\alpha$-picoline, $\beta$-picoline).

Another group of bases which are suitable for carrying out the process of the invention consists of phosphines.

Trialkyl- and triarylphosphines are preferably used. Mention may be made in particular of trimethylphosphine, triethylphosphine, tri-n-propylphosphine, tri-n-butylphosphine, tricyclohexylphosphine, triphenylphosphine and tritolylphosphine.

Examples of catalysts which are entirely suitable for carrying out the invention are given below:

pyridinium tosylate, ammonium itaconate, pyridinium itaconate, pyridinium hydrochloride, phosphinium hydrobromide.

The amount of catalyst used in the process of the invention is such that it represents from 0.1 to 30%, preferably from 1 to 4%, of the weight of the itaconic acid.

In accordance with the process of the invention, the catalyst may be introduced in solid form, at the same time as the itaconic acid, which is in solid form.

With the catalyst being soluble under the reaction conditions, it is desirable to melt it before introducing it.

It is also possible to use the catalyst separately, dissolved in water or in an organic solvent such as those mentioned above.

The temperature at which the reaction is carried out is such that the itaconic acid is liquid in the medium. It is at least about 130° C.

The temperature is advantageously chosen within a temperature range from 130° C. to 180° C., preferably from 150° C. to 170° C.

The reaction is advantageously performed at atmospheric pressure.

In the case where the organic solvent has too low a boiling point, it is possible to carry out the process of the invention under pressure.

In the reverse case, in which the solvent has too high a boiling point, the process of the invention may be performed under a reduced pressure advantageously of between 100 mm (13300 Pa) and 500 mm (46500 Pa) of mercury.

According to a preferred variant of the process of the invention, the process of the invention is carried out under a controlled atmosphere of inert gases. An atmosphere of rare gases, preferably argon, may be established, but it is more economical to use nitrogen.

From a practical point of view, the reaction is easily carried out.

A first embodiment consists in carrying out the process of the invention in a stirred reactor or in a cascade of reactors.

The source of itaconic acid, in solid form or in solution, is introduced continuously into the reaction medium maintained at a temperature such that it is liquid.

The supply of itaconic acid is such that its residence time in the reaction medium is from 0.5 to 5 hours.

As mentioned above, a catalyst may be added either with itaconic acid, in solid form, or in solution in water or a solvent, but in a separate manner.

When the water formed by the reaction is eliminated by azeotropic distillation, this elimination is performed continuously.

The citraconic anhydride produced is removed continuously, by any known means, in particular by overflowing.

Another practical embodiment of the invention consists in carrying out the process of the invention in a distillation column.

The source of itaconic acid and the catalyst are introduced at the top of a column with plates.

The number of plates and the volume of each plate must be such that the residence time of the itaconic acid is between 0.3 and 3 hours. The column is heated at the base so as to recover, at the head, the water of reaction in the form of an azeotropic mixture with the solvent. This water is allowed to separate by settling and is removed continuously. At the foot of the column, a solution of citraconic anhydride in the solvent is removed in order to maintain a constant level.

The water of the water/organic solvent binary azeotrope may be eliminated either by passing the said azeotrope over a solid which absorbs water such as, for example, molecular sieves, before recycling, or may be eliminated by separation after settling has taken place.

The citraconic anhydride is recovered by the conventional means used in this technical field, preferably by distillation or extraction.

Another subject of the invention is to make use not of pure or semi-pure itaconic acid but to use the fermentation broth of itaconic acid or of by-products in the manufacture of itaconic acid, in particular waste waters, as a source of itaconic acid.

The viability of the process is considerably improved. The reason for this is that the price of itaconic acid is a deciding factor on the cost of the anhydride produced.

As already indicated, itaconic acid is obtained by fermentation of sugar solutions by means of a fungus often belonging to the Aspergillus family.

In order to isolate the itaconic acid from the fermentation broth, it is necessary to remove the fungus by filtration and then to purify by the means well known to those skilled in the art, in order to obtain pure itaconic acid.

These purifications are complicated and require considerable equipment means in order to be successfully carried out. In addition, the yield is never excellent. All these reasons explain why the price of pure itaconic acid is very high and clearly demonstrate the economy achieved according to the process of the invention, starting from residues from the manufacture of itaconic acid, since in this case the starting material is free and the amount of pollution is reduced by upgrading a residue to a valuable product.

In accordance with the invention, fermentation broth may be used as starting material to manufacture citraconic anhydride, rather than pure or semi-pure itaconic acid.

The itaconic acid is obtained by aerobic fermentation of a nutrient medium which contains a hydrocarbon source, a nitrogen source and trace elements, by means of a microorganism belonging to the strain of Aspergillus producing itaconic acid.

The hydrocarbon source used may be of diverse origin. They are generally carbohydrates, the most frequently used of which include mono- and disaccharides such as glucose, sucrose, fructose, starches provided that they are in a form which can be assimilated by the microorganism, and beet molasses.

Use may also be made of glycerol as a hydrocarbon source, in accordance with FR-A-2,702,492.

In the case where starch is used as the carbon source, it is advantageous to add a saccharifying amylolytic enzyme as described in EP-A-0,341,112.

For the formulation of the corresponding nutrient media, a concentration of carbon substrate which is in the range between 50 and 200 g/l, expressed on a weight per unit volume basis, is preferably used according to the invention.

The nitrogen source may be chosen in particular from metabolizable organic or inorganic compounds, such as the soluble extract of maize ("corn steep liquor") and/or of soya, urea, ammonium sulphate, ammonium chloride, ammonium phosphate, ammonium nitrate, etc. and mixtures thereof.

The medium also contains inorganic salts such as sulphates, chlorides or phosphates of Ca, Mg, Na, K, Fe, N, Co, Cu, Mn or Zn as well as other usual additives such as pH-controlling agents and/or anti-foaming agents.

As microorganisms which can be used according to the invention, mention will be made most particularly of the species *Aspergillus terreus* and *Aspergillus itaconicus*.

The microorganism is more particularly *Aspergillus terreus* and preferably the strain NRRL 1960 identified in patent EP-A-341,112.

The microorganism is introduced into the fermentation medium in a manner which is conventional per se, using an inoculum or intermediate cultures.

The fermentation is conveniently performed at an acidic pH within the range approximately between 1.8 and 5 and at a temperature from approximately 20° C. to approximately 40° C.; the optimum conditions depend on the specific strain of the microorganism employed.

The broth is stirred and aerated, at a temperature chosen within the abovementioned range, for 3 to 7 days.

A fermentation broth with an itaconic acid assay of 5 to 20% by weight is recovered.

The process of the invention then consists:

in removing the mycelium from the fermentation broth containing the itaconic acid, in placing, if necessary, the itaconic acid in free acid form, by an acidic treatment, in optionally concentrating the fermentation broth and extracting it with a suitable solvent, in carrying out the dehydration/isomerization step as described, in recovering the citraconic anhydride obtained.

In a first step, the fermentation broth is freed of the mycelium according to the standard techniques of solid/liquid separation, preferably by filtration or by centrifugation.

When an organic acid is produced by fermentation, it is at least partially present in the combined state, in particular in the form of salts. It can conveniently be liberated by an acidic treatment.

To this end, a strong inorganic acid is added, preferably sulphuric acid, hydrochloric acid, nitric acid or phosphoric acid.

The amount of acid added is such that the pH is lowered to a value below or equal to about 5, preferably between 1.5 and 5, and even more preferably between 2 and 2.5.

It is desirable to concentrate the fermentation broth.

To do this, it is concentrated by heating to a temperature of between 50° C. and 110° C., at atmospheric pressure or under a reduced pressure advantageously of between 100 mm (13300 Pa) and 500 mm (46500 Pa) of mercury.

The broth obtained has an itaconic acid concentration of from 20 to 80% by weight, preferably of from 30 to 50% by weight.

A solvent which is sparingly soluble in water and which forms an azeotrope with it is then added, optionally along with a catalyst, and the dehydration/isomerization is continued.

The above description may be referred to for examples of preferred catalysts, solvents and conditions for the process.

A solution of citraconic anhydride in the solvent is obtained.

This solution is then distilled in order to recover the solvent, which is recycled, and the citraconic anhydride.

The various impurities which do not have the itaconic or citraconic structure and which are present in the starting broth remain after recovery of the citraconic anhydride. They are incinerated.

In the case where the broth containing the itaconic acid is of poor quality (that is to say that it contains large amounts of inorganic or organic impurities such as, for example, salts and sugars), in order to reduce the technological problems associated with the elimination of heavy fractions during the final distillation of the citraconic anhydride, it is is preferable, without this being absolutely obligatory, to extract the itaconic acid with a suitable solvent or mixture of solvents.

Conventional solvents for extracting organic acids are used. Examples which may be mentioned are the following solvents, used alone or as mixtures: ketones such as methyl ethyl ketone, methyl isobutyl ketone, diisobutyl ketone, methyl n-amyl ketone, methyl isoamyl ketone, cyclohexanone, methylcyclohexanone and diacetone alcohol; chlorinated aliphatic hydrocarbons such as dichloromethane, trichloromethane, carbon tetrachloride and dichloroethane; oxide ethers such as, for example, propyl ether or, preferably, isopropyl ether, as a mixture with a ketone.

The volume of organic solvent generally represents from 0.5 to 4 times the volume comprising the compound to be extracted.

The resulting organic layer is concentrated as above in order to recover the solvent, the dehydration/isomerization being carried out as indicated above.

Another variant for carrying out the invention consists in performing the dehydration/isomerization reaction directly in the organic layer and then in concentrating the citraconic anhydride solution obtained.

The latter technique is the one preferably adopted for the manufacture of citraconic anhydride from residual waters which are by-products from the purification of itaconic acid.

Their composition is, obviously, very variable and it may be pointed out, by way of example, that they generally contain from 10 to 50% by weight of solids which are distributed as follows:

from 5 to 30% of non-fermentable residues or hydrocarbon sources,
from 1 to 10% of inorganic salts,
from 5 to 20% of tars and various heavy fractions,
from 5 to 25% of itaconic acid.

All the operations described above use a fermentation broth or a broth of production residues as the source of itaconic acid, and they may be performed either in a batchwise manner or continuously. Although the batchwise process is very flexible and is widely used for small- or medium-scale productions, the performance becomes far poorer when large-scale productions are involved. The continuous implementation is thus preferred.

The examples which follow illustrate the invention without, however, limiting it.

In the examples, the percentages given are by weight except where otherwise mentioned.

EXAMPLES

Example 1

Manufacture from a broth concentrated simply.

2000 kg of mycelium-freed broth with an itaconic acid titre of 9.1%, assayed by high performance liquid chromatography, are taken.

Concentration to 108° C. is performed in the mass, distilling off all of the water formed.

An equal weight of pseudocumene solvent and 5 g of catalyst (pyridinium phosphate) are added to the liquid obtained.

The water is distilled off at atmospheric pressure until no more comes off.

An organic solution containing 28.2 g of citraconic anhydride, assayed by high performance liquid chromatography, is obtained.

The yield of citraconic anhydride based on the itaconic acid assayed in the starting broth is 18%.

Example 2

Use of a strong acid before reaction.

The process is performed as in Example 1, adding to the broth 3% concentrated sulphuric acid relative to the itaconic acid assayed, the other operations being identical.

An organic solution containing 119 g of citraconic anhydride, assayed by high performance liquid chromatography, is obtained.

The yield of citraconic anhydride based on the itaconic acid assayed in the starting broth is 76%.

Example 3

Identical to Example 2 with cyclohexanone solvent.

2000 kg of mycelium-freed broth are taken (itaconic acid titre 9.1% by high performance liquid chromatography).

3% of sulphuric acid relative to the itaconic acid assayed are added, followed by concentration to 108° C. in the mass, distilling all of the water which forms.

The liquid obtained, maintained at 90°–98° C., is supplied over 3 hours on an identical amount of cyclohexanone solvent and 5 g of catalyst (pyridinium phosphate).

The water is distilled off at atmospheric pressure until no more comes off.

An organic solution containing 117 g of citraconic anhydride, assayed by high performance liquid chromatography, is obtained.

The yield of citraconic anhydride based on the itaconic acid assayed in the starting broth is 75%.

Example 4

Continuous manufacture starting with pure itaconic acid.

200 kg/h of pure molten itaconic acid, 200 kg/h of pseudocumene and 1 kg/h of pyridinium para-toluenesulphonate catalyst are supplied into a heated stirred reactor with a volume of 1 m$^3$, fitted with a column with plates.

The water of reaction is drawn off at the head while recycling the organic layer.

At the foot, a pseudocumene/citraconic anhydride mixture is withdrawn so as to keep the level in the reactor constant.

Under stabilized conditions, a high performance liquid chromatographic assay gives 143 kg/h of citraconic anhydride in the solution coming off at the foot of the reactor, which corresponds to a yield of 83% relative to the itaconic acid supplied.

Example 5

Identical to Example 4 with a lighter solvent.

The process is performed as in Example 4, replacing the pseudocumene solvent by xylene introduced into the reactor, so as to keep the bulk temperature within the range 160° C. –170° C.

The yield of citraconic anhydride assayed relative to the pure itaconic acid supplied is 84%.

Example 6

Continuous manufacture starting with residue.

The itaconic acid purification residue has the following composition:

10% itaconic acid,

14% various sugars,

10% various heavy fractions,

5% inorganic salts, remainder to 100% being water.

The said residue is supplied at a rate of 220 kg/h into a liquid/liquid extraction column which is also supplied in counter-current with 600 l/h of a methyl ethyl ketone/isopropyl ether mixture at a ratio by volume of 80/20.

An organic solution is recovered, which is continuously concentrated in a distillation column supplied with water, at the base of which a water/itaconic acid mixture containing 30% itaconic acid is recovered (temperature 108° C., flow rate 20.9 kg/h of 100% acid).

This solution is continuously concentrated on a falling film evaporator, so as to obtain a solution containing 60% itaconic acid.

This solution (34.8 kg/h) is continuously supplied into a stirred reactor (volume 100 litres) equipped for distillation.

It is supplied therein at the same time as 21 kg/h of pseudocumene solvent and 0.8 kg/h of catalyst (pyridinium para-toluenesulphonate).

The water of reaction and that introduced by the reactants are drawn off at the head and a solution of citraconic anhydride in the solvent is withdrawn at the foot.

High performance liquid chromatographic assay shows that, under stabilized conditions, 14.4 kg/h of citraconic anhydride are produced, which corresponds to a yield of 76% relative to the acid assayed in the starting residue.

Example 7

Identical to Example 6. starting with a fermentation broth.

The process is performed as in Example 6, replacing the production residue used as starting material by a mycelium-freed broth containing 9.1% itaconic acid assayed by high performance liquid chromatography (flow rate 220 kg/h).

Under established conditions, 13.4 kg/h of citraconic anhydride are obtained, which corresponds to a yield of 78%.

Example 8

Starting with a concentrated fermentation broth.

A fermentation broth containing 10.1% itaconic acid is freed of the mycelium and then concentrated at atmospheric pressure to 33% acid (assay by high performance liquid chromatography).

This solution is supplied at a rate of 200 kg/h to a liquid/liquid extraction column which is also supplied in counter-current with 500 l/h of a methyl ethyl ketone/isopropyl ether mixture at a ratio by volume of 80/20.

An organic solution is recovered, which is continuously concentrated in a distillation column supplied with water, at the base of which a water/itaconic acid mixture containing 33% itaconic acid is recovered (temperature 109° C., flow rate 65 kg/h of 100% acid).

This solution is continuously concentrated on a falling film evaporator so as to obtain a solution containing 60% itaconic acid. This solution (108 kg/h) is continuously supplied into a stirred reactor equipped for distillation.

It is supplied therein at the same time as 49 kg/h of pseudocumene solvent and 0.4 kg/h of catalyst (pyridinium para-toluenesulphonate).

The water of reaction and that introduced by the reactants are drawn off at the head and a solution of citraconic anhydride in the solvent is withdrawn at the foot.

High performance liquid chromatographic assay shows that, under stabilized conditions, 45.3 kg/h of citraconic anhydride are produced, which corresponds to a yield of 81% relative to the acid assayed in the starting broth.

Example 9

Starting with residue, extraction with methyl ethyl ketone alone.

The process is performed as in Example 6, using pure methyl ethyl ketone instead of the methyl ethyl ketone/isopropyl ether mixture.

The yield of citraconic anhydride assayed by high performance liquid chromatography is 48%.

Example 10

Manufacture starting with broth without prior concentration.

200 kg/h of filtered itaconic broth with a titre of 9.1% itaconic acid, assayed by high performance liquid chromatography, are supplied into a liquid/liquid extraction column equivalent to 2.9 theoretical plates.

In parallel, 112 kg/h of a cyclohexanone/isopropyl ether mixture are supplied at the base (10% isopropyl ether content).

An organic solution containing 18.0 kg of itaconic acid, assayed by high performance liquid chromatography, is recovered at the head. 0.2 kg/h of catalyst (aqueous solution containing 50% triethanolamine phosphate) is added continuously to this solution.

This solution is supplied to the head of a column with plates, 0.2 metre in diameter, containing 5 bell plates and a boiling vessel, the latter having a volume of 25 litres.

This column is heated by a coil supplied with steam at 12 bar.

The vapours emerging at the head of the column are condensed, the liquid being separated out after settling has taken place (aqueous layer and organic layer, cyclohexanone and isopropyl ether mixture).

A solution of citraconic anhydride in cyclohexanone is collected at the foot of the column, so as to keep the level constant, at a flow rate of 23.2 kg/h and with a titre of 50.0% citraconic anhydride.

The yield of citraconic anhydride is 75% relative to the acid assayed in the broth.

What is claimed is:

1. A process for the preparation of citraconic anhydride in a reaction medium, continuously or in a batchwise manner, comprising the steps of:

introducing itaconic acid or a starting material comprising it, into the reaction medium wherein the source of itaconic acid is a fermentation broth or a production residue comprising itaconic acid, said process being carried out in the presence of a catalyst, and wherein the catalyst is a salt prepared at the time of use or in situ by reaction of itaconic acid and a base.

2. A process for the preparation of citraconic anhydride in a reaction medium, continuously or in a batchwise manner, comprising the steps of:

introducing itaconic acid or a starting material comprising it, into the reaction medium wherein the source of itaconic acid is a fermentation broth or a production residue comprising itaconic acid, said process being carried out in the presence of a catalyst, and wherein the catalyst is prepared from an halogenated acid selected from the group consisting of hydrochloric acid, hydrobromic acid and hydrofluoric acid.

3. A process for the preparation of citraconic anhydride in a reaction medium, continuously or in a batchwise manner, comprising the steps of:

introducing itraconic acid or a starting material comprising it, into the reaction medium wherein the source of itaconic acid is a fermentation broth or a production residue comprising itaconic acid, said process being carried out in the presence of a catalyst, and wherein the catalyst is prepared from an oxyacid selected from the group consisting of sulphuric acid, pyrosulphuric acid, perchloric acid and phosphoric acid.

4. A process for the preparation of citraconic anhydride in a reaction medium, continuously or in a batchwise manner, comprising the steps of:

introducing itaconic acid or a starting material comprising it, into the reaction medium wherein the source of itaconic acid is a fermentation broth or a production residue comprising itaconic acid, said process being carried out in the presence of a catalyst, and wherein the catalyst is selected from the group consisting of:

pyridinium tosylate, ammonium itaconate, pyridinium itaconate, pyridinium hydrochloride, and phosphinium hydrobromide.

5. A process for the preparation of citraconic anhydride in a reaction medium, continuously or in a batchwise manner, comprising the steps of:

introducing itaconic acid or a starting material comprising it, into the reaction medium wherein the source of itaconic acid is a fermentation broth or a production residue comprising itaconic acid, said process being carried out in the presence of a catalyst, and said process further comprising the use of of an organic solvent having a boiling point of between 110° C. and 200° C., wherein the organic solvent is selected from the group consisting of:

aliphatic hydrocarbons, chlorinated aliphatic hydrocarbons, ethers, nitro compounds, aliphatic ketones, cycloaliphatic ketones, and aromatic ketones.

* * * * *